(12) United States Patent
Straayer et al.

(10) Patent No.: US 10,362,999 B1
(45) Date of Patent: Jul. 30, 2019

(54) GATED PHYSIOLOGIAL MONITORING SYSTEM AND METHOD

(71) Applicant: Maxim Integrated Products, Inc., San Jose, CA (US)

(72) Inventors: Matthew Z. Straayer, Acton, MA (US); Joohyun Seo, Cambridge, MA (US)

(73) Assignee: MAXIM INTEGRATED PRODUCTS, INC., San Jose, CA (US)

( * ) Notice: Subject to any disclaimer, the term of this patent is extended or adjusted under 35 U.S.C. 154(b) by 11 days.

(21) Appl. No.: 15/332,255

(22) Filed: Oct. 24, 2016

Related U.S. Application Data

(60) Provisional application No. 62/246,012, filed on Oct. 24, 2015.

(51) Int. Cl.
| | | |
|---|---|---|
| *A61B 5/02* | (2006.01) | |
| *A61B 5/00* | (2006.01) | |
| *A61B 5/11* | (2006.01) | |
| *A61B 5/024* | (2006.01) | |
| *A61B 5/0402* | (2006.01) | |
| *A61B 5/1455* | (2006.01) | |
| *A61B 5/053* | (2006.01) | |

(52) U.S. Cl.
CPC ........ *A61B 5/7285* (2013.01); *A61B 5/02416* (2013.01); *A61B 5/0402* (2013.01); *A61B 5/1102* (2013.01); *A61B 5/14551* (2013.01); *A61B 5/053* (2013.01)

(58) Field of Classification Search
CPC . A61B 5/7285; A61B 5/02416; A61B 5/0402; A61B 5/1102; A61B 5/14551; A61B 5/053
See application file for complete search history.

(56) References Cited

U.S. PATENT DOCUMENTS

| | | | |
|---|---|---|---|
| 8,571,622 B2 | 10/2013 | Huiku et al. | |
| 8,617,080 B2 | 12/2013 | Turcott | |
| 9,241,643 B2 | 1/2016 | Lisogurski et al. | |
| 2011/0009754 A1* | 1/2011 | Wenzel | A61B 5/0215 600/485 |
| 2012/0053432 A1* | 3/2012 | Huiku | A61B 5/14551 600/324 |
| 2012/0203077 A1* | 8/2012 | He | A61B 5/02055 600/301 |
| 2015/0148637 A1 | 5/2015 | Golda et al. | |

OTHER PUBLICATIONS

Desjardins, Benoit et al., "ECG-Gated Cardiac CT", American Journal of Roentgenology, vol. 182, No. 4, Apr. 2004, pp. 1-43.

* cited by examiner

*Primary Examiner* — Eric J Messersmith
(74) *Attorney, Agent, or Firm* — Kevin E. West

(57) ABSTRACT

Gated physiological monitoring systems and methods are described that utilize a photoplethysmogram (PPG) monitoring device and another (different) physiological monitoring device, where the PPG monitoring device is operated based on timing information obtained from the other physiological monitoring device. In some implementations, control circuitry can be configured to operate the PPG monitoring device based on timing information from a physiological waveform detected by the physiological monitoring device. For example, the control circuitry can operate the PPG monitoring device to capture one or more selected portions of a measured PPG waveform that can then be used to estimate the full PPG waveform or portions of interest.

20 Claims, 6 Drawing Sheets

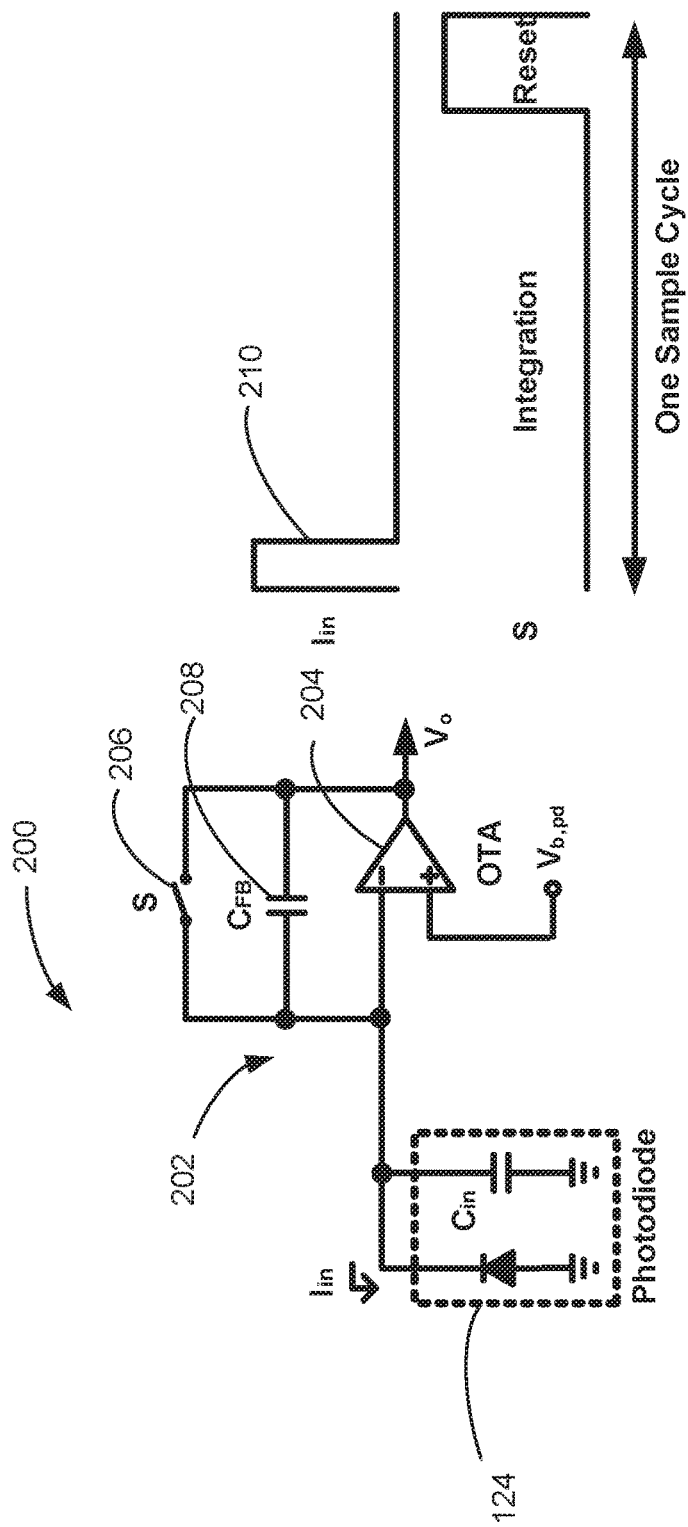

GATED PHYSIOLOGIAL MONITORING SYSTEM AND METHOD

CROSS-REFERENCE TO RELATED APPLICATIONS

The present application claims the benefit under 35 U.S.C. § 119(e) of U.S. Provisional Application Ser. No. 62/246,012, filed Oct. 24, 2015, and titled "GATED PHYSIOLOGICAL MONITORING SYSTEM AND METHOD," which is incorporated herein by reference in its entirety.

BACKGROUND

Vital signs such as heart rate, oxygen saturation (SpO2), temperature, and blood pressure constitute basic assessments of patients' health in clinical environment. These vital signs are either directly measured or indirectly extracted from physiological waveforms such as electrocardiogram (ECG) and photoplethysmogram (PPG). While these vital signs are continuously monitored in an in-patient ward, they are highly under-sampled for out-patients as they are mainly obtained at clinics or hospitals not at home or the workplace. Recently, several wearable vital sign monitors have been introduced with the advancement of wearable sensor nodes as well as the reduction of their form factor. At the same time, the battery operated wearable monitor significantly constrains a power budget because the power consumption of the monitor mainly determines the maximum operating time without replacing the battery.

SUMMARY

Gated physiological monitoring systems and methods are described that utilize a photoplethysmogram (PPG) monitoring device and another (different) physiological monitoring device, where the PPG monitoring device is operated based on timing information obtained from the other physiological monitoring device. In some implementations, a data converter (e.g., analog-to-digital converter (ADC)) receives information (e.g., electrical signals corresponding to physiological measurements) from the physiological monitoring device, converts the information into data (e.g., a discrete or digital format), and transmits the data to control circuitry (e.g., a processor, microcontroller, programmable logic device, ASIC, or the like). The control circuitry can be configured to operate the PPG monitoring device based on the data received from the data converter. In some implementations, the control circuitry can be configured to operate the PPG monitoring device based on timing information from a physiological waveform detected by the physiological monitoring device. For example, the control circuitry can operate the PPG monitoring device to capture one or more selected portions of a measured PPG waveform that can then be used to estimate the full PPG waveform or portions of interest.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

FIG. 2A is a block diagram of a portion of circuitry for the gated physiological monitoring system in accordance with an embodiment of this disclosure, where the circuitry includes a trans-impedance amplifier.

FIG. 2B shows examples of an LED signal and a waveform illustrating a state of a switch in the portion of circuitry shown in FIG. 2A.

DETAILED DESCRIPTION

Overview

Figure 1A:
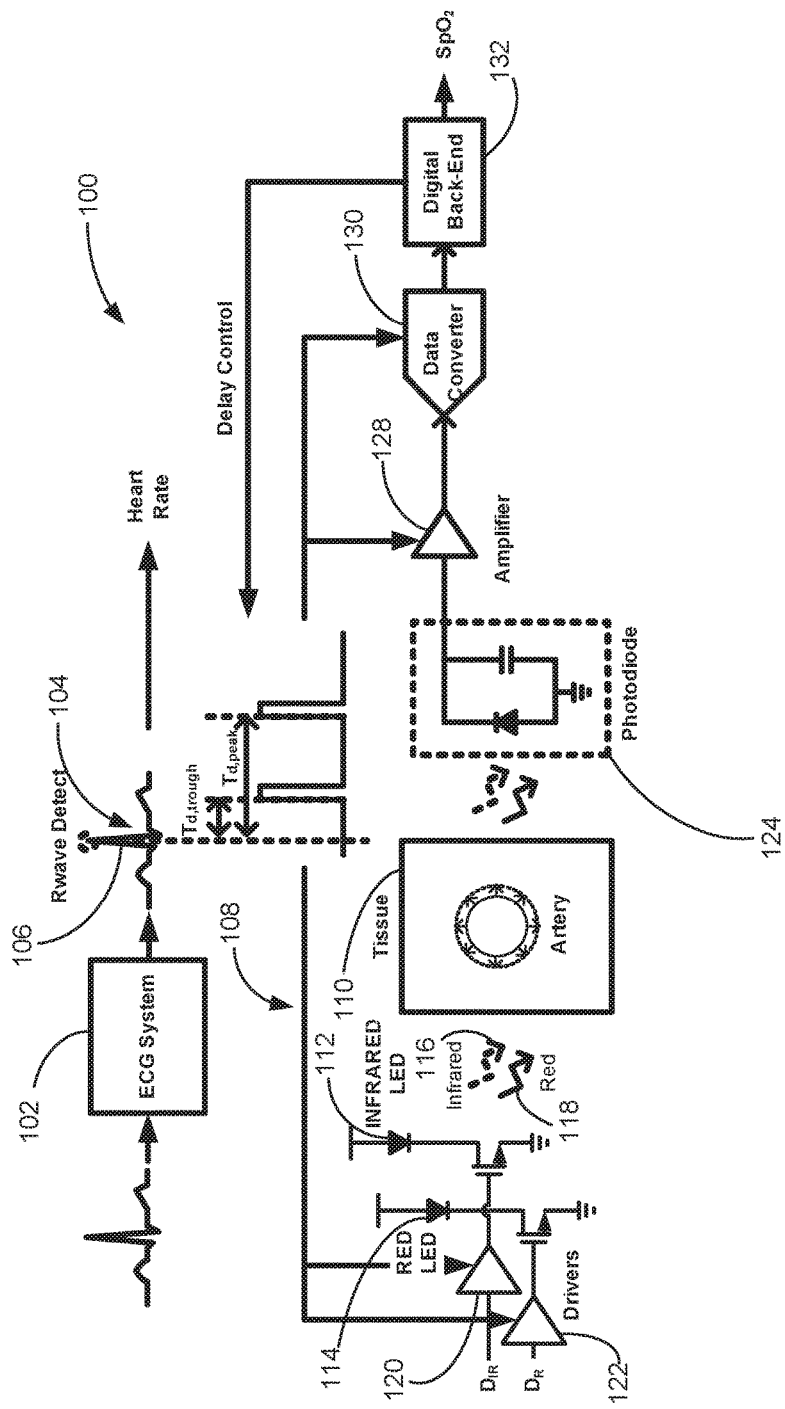
FIG. 1A is a block diagram of a gated physiological monitoring system in accordance with embodiments of the present disclosure.

Among various vital signs, the measurement of SpO2 costs significant power consumption because the measurement involves emitting red (660 nm wavelength) and infrared (940 nm wavelength) light. On the other hand, the measurement of an ECG signal costs much smaller power because the measurement system is a passive read-out circuitry of a bio-potential at the body surface. Therefore, the measurement of SpO2, called pulse oximetry, becomes a bottleneck to increase the maximum operating time of the wearable vital sign monitors. Power consumption of a pulse oximetry system can be reduced with systems and techniques described herein.

The SpO2 measurement usually requires a PPG waveform which is a modulated light signal due to arterial pulsation. When light is propagated to medium such as tissue and blood, the intensity of light is attenuated exponentially. Therefore, as the artery extends and contracts during a cardiac cycle, a transmitted light signal at the other end is being modulated. In addition, the rate of attenuation per unit length is characterized by a medium dependent parameter called absorbance, and depending on hemoglobin oxygenation level, arterial absorbance also changes, providing a basis to determine different SpO2 level. While transmittance pulse oximetry is described, the same principle holds for reflectance pulse oximetry, which is usually utilized for wearable monitors, except lights are now propagated and scattered back to the sensor instead of transmitting all the way to the other end of medium.

Traditionally, the measurement of the PPG waveform is achieved by utilizing an electronic processor and shining light-emitting diodes (LEDs) on tissue. Oxygenated hemoglobin absorbs more infrared light and allows more red light to pass through. Deoxygenated hemoglobin allows more infrared light to pass through and absorbs more red light. The amount of light that is transmitted (e.g., not absorbed) or reflected is measured, and separate normalized signals are produced for each wavelength. These signals fluctuate in time because the amount of arterial blood that is present increases (literally pulses) with each heartbeat. The light transmitted or reflected is detected at photodiodes and converted to a light dependent current signal. The current signal is then conditioned in analog and digital domains to generate the PPG signal. Then, SpO2 estimation consists of calculating a parameter called ratio of ratios (Λ) which is given by:

$$\Lambda = \frac{\frac{AC_R}{DC_R}}{\frac{AC_{IR}}{DC_{IR}}} = \frac{\frac{PPG_{R,max} - PPG_{R,min}}{PPG_{R,max} + PPG_{R,min}}}{\frac{PPG_{IR,max} - PPG_{IR,min}}{PPG_{IR,max} + PPG_{IR,min}}}$$

$$SpO_2(\%) = \frac{81 - 18\Lambda}{0.73 + 0.11\Lambda}$$

and estimating SpO2 based on the knowledge of the absorbances of oxygenated and deoxygenated hemoglobin at red and infrared lights. The exact coefficients can often be calibrated. Although this conventional architecture provides a full PPG waveform, the continuous operation of LEDs results in significant power consumption.

In order to reduce the LED power consumption, either the intensity of LED light or the average on-time of LED should be reduced. Some PPG monitoring devices that adaptively control the intensity of LED light in various conditions while maintaining the sufficient signal-to-noise ratio (SNR) of a detected signal. The SNR of the detected signal is estimated in an SNR estimation block, and the strength of LED drivers is controlled such a way that the SNR is maintained just high enough to achieve certain level of accuracy in the SpO2 estimation. Given that the conventional architecture is conservatively designed for a worst case scenario, this architecture may provide a chance to reduce unnecessary power consumption of LEDs in certain environmental situations.

In order to decrease the average on-time of LEDs to reduce power consumption, some PPG monitoring devices incorporate a LED light chopping with a frequency much higher than a signal bandwidth. In this architecture, an LED operation is duty-cycled (2-10%), and red and infrared lights are alternatively shined on the tissue. The detected light signal at the photodiode is a pulse train whose amplitude is modulated by arterial pulsation. Then a low-pass filter rejects high frequency contents originated from the fast LED light chopping and only leaves a low-frequency PPG signal.

This architecture introduces the extra complexity of designing a low-pass filter in a signal chain and LED drivers with sufficient bandwidth to achieve a fast LED on-off operation. The low pass filter can be implemented in an analog domain followed by a data converter running at a low speed in a subsequent stage. However, a high-order analog low pass filter with the cut-off frequency of a few hertz (Hz) can be challenging to design. In addition, the amplifier is now required to have wider bandwidth than the traditional architecture such that the light dependent current signal can settle within an LED-on duration. Overall, the complexity and power consumption of photoreceptor circuitries increase but the reduction of LED power consumption is substantial to justify extra design overheads. Moreover, this architecture still provides a full PPG waveform that can be utilized to estimate pulse rate. However, the power consumption of this system still ranges from several hundreds of μWs to several mWs, which is excessively high to realize several months of operation or even complete energy autonomy based on ambient energy harvesting.

The most valuable information about heart rate and oxygen saturation is concentrated on the specific part of the PPG waveform. When calculating the ratio-of-ratios, it is desirable to have values of PPG at its minimum (trough) and maximum (peak) where maximum AC value can be obtained. In heart rate estimation, the upstroke of the PPG waveform at the beginning of a cardiac cycle provides the most valuable information. Some PPG monitoring devices utilize adaptive sampling in addition to LED light chopping to further reduce the power consumption of LEDs while preserving the part of the PPG waveform that contains essential information to estimate SpO2 and heart rate. In this architecture, LEDs are initially operating in the same manner as the architecture presented above, with LED drivers with sufficient bandwidth to achieve a fast LED on-off operation. Once the heart rate is identified from a full PPG waveform, LED drivers are periodically disabled when non-essential information is present. The remaining of the PPG waveform can still be utilized for heart rate estimation, which provides timing information about when to disable the LED drivers in subsequent cardiac cycles. In this architecture, a linear filter cannot be employed in a signal chain due to the nature of adaptive sampling, which may hurt SNR because a noise bandwidth cannot be completely equalized to a signal bandwidth. Still, the significant reduction of LED power consumption can justify extra power consumption at the receiver circuitry to achieve sufficient SNR. Although this architecture offers another LED power reduction from the LED chopping technique, the robustness of operation is challenged by the relatively high beat-to-beat variability of heart rate. In order to be more robust, LEDs must operate longer to still preserve the part of the PPG waveform even if the estimated heart rate from previous cardiac cycles is far different from the real heart rate of a current cycle.

In this disclosure, gated physiological monitoring systems and methods are described that utilize a photoplethysmogram (PPG) monitoring device and another (different) physiological monitoring device, where the PPG monitoring device is operated based on timing information obtained from the other physiological monitoring device. In some implementations, a data converter (e.g., analog-to-digital converter (ADC)) receives information (e.g., electrical signals corresponding to physiological measurements) from the physiological monitoring device, converts the information into data (e.g., a discrete or digital format), and transmits the data to control circuitry (e.g., a processor, microcontroller, programmable logic device, ASIC, or the like). The control circuitry can be configured to operate the PPG monitoring device based on the data received from the data converter. In some implementations, the control circuitry can be configured to operate the PPG monitoring device based on timing information from a physiological waveform detected by the physiological monitoring device. For example, the control circuitry can operate the PPG monitoring device to capture one or more selected portions of a measured PPG waveform that can then be used to estimate the full PPG waveform or portions of interest.

Example Implementations

FIG. 1A illustrates a gated physiological monitoring system 100 in accordance with an embodiment of the present disclosure. The gated physiological monitoring system 100 includes a physiological monitoring device (e.g., an ECG system 102). The ECG system 102 includes a sensor that can detect a physiological waveform other than a PPG waveform (e.g., an ECG signal 104). Heart rate can be directly measured form the QRS complex of the ECG signal using various detector methods (e.g., Pan-Tompkins algorithm, or the like). The ECG system 102 can utilize the QRS complex to detect the R-wave 106 in the ECG signal. The ECG system 102 (or associated control circuitry) can generate timing information from the detected R-wave 106. However, the use of an ECG system 102 is offered by way of example only and is not meant to be restrictive of the present disclosure. In other embodiments, other physiological waveforms that provide information about arterial pulsation can be used (e.g., ballistocardiogram, impedance cardiogram, etc.).

Figure 1B:
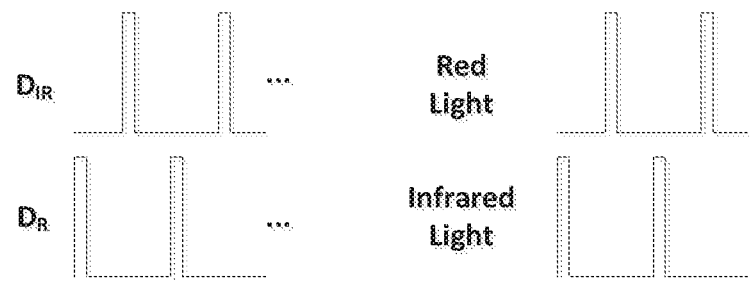
FIG. 1B shows examples of LED waveforms for red light and infrared light supplied for the gated physiological monitoring system of FIG. 1A.

The gated physiological monitoring system 100 also includes a PPG monitoring device 108. The PPG monitoring device 108 is configured to propagate at least one wavelength of light (e.g., infrared, red, etc.) into a subject's tissue 110. In some embodiments, the PPG monitoring device 108 can include one or more light emitters and one or more drivers. For example, the one or more light emitters can be an infrared light emitting diode (LED) 112 and a red LED 114. The infrared LED 112 and the red LED 114 can propagate infrared light 116 and red light 118, respectively. The one or more drivers can include an infrared LED driver 120 and a red LED driver 122 coupled to the infrared LED 112 and the red LED 114, respectively. The infrared LED driver 120 and the red LED driver 122 can propagate the infrared light 116 and the red light 118, respectively, to a medium (e.g., tissue 110). Example light signals/waveforms for the infrared light and red light are shown in FIG. 1B. The use of red and infrared light is offered by way of example only and is not meant to be restrictive of the present disclosure. For example, light used can include one or more of ultrasound, radio, microwave, millimeter wave, infrared, visible, ultraviolet, gamma ray, or X-ray electromagnetic radiation.

Figures 1C, 1D:
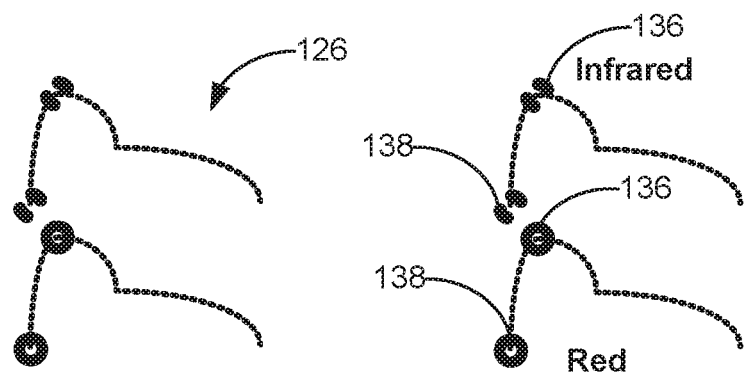
FIG. 1C shows examples of light dependent current signals detected from red light and/or infrared light transmitted through or reflected from tissue of a subject under analysis of the gated physiological monitoring system of FIG. 1A.
FIG. 1D shows examples of PPG waveforms based on the light dependent current signals of FIG. 1C.

The PPG monitoring device 108 can also include at least one light detector (e.g., photodiode 124, or the like). The photodiode 124 can sense at least one of the infrared light 116 or the red light 118 transmitted or reflected from the tissue 110. In implementations, the photodiode 124 can convert the infrared light 116 and/or the red light 118 to at least one light dependent current signal 126 (e.g., as shown in FIG. 1C). The detection of infrared light 116 and red light 118 is offered by way of example only and is not meant to be restrictive of the present disclosure. In other embodiments, the detector can be used to sense any wavelength within the radio, microwave, infrared, visible, ultraviolet, X-ray, or electromagnetic spectra. In embodiments, the PPG monitoring device 108 can further include an amplifier 128. The amplifier 128 can receive the at least one current signal 126 from the photodiode 124 and translate the at least one current signal 126 into a PPG voltage signal (e.g., as shown in FIG. 1D).

FIG. 2A illustrates a portion of circuitry 200 for the gated physiological monitoring system 100 in accordance with an embodiment of this disclosure, where the circuitry includes a trans-impedance amplifier 202. The trans-impedance amplifier 202 can be used to control the SNR. The trans-impedance amplifier 202 can include an operational trans-conductance amplifier 204. The trans-impedance amplifier 202 presents a low impedance to the photodiode 124 and isolates it from the output voltage of the operational trans-conductance amplifier 204. The trans-impedance amplifier 202 also includes a switch 206 and a feedback capacitor 208. The switch 206 is synchronized to the one or more LEDs (e.g., synchronized to a light signal, such as the light signal as shown in FIG. 2B). Initially, the switch 206 can be closed to reset the trans-impedance amplifier 202 and reverse-bias the photodiode 124 for a proper mode of operation. When a light pulse 210 is present, the switch 206 can open, and the at least one current signal 126 is thereby integrated by the feedback capacitor 208. The light remains on for a short period of time (e.g., pulse 210), allowing the current signal 124 to be almost constant. The output voltage 212 of the trans-impedance amplifier 202 becomes proportional to the current signal 124. In order to limit the noise bandwidth of the operational trans-conductance amplifier 204, the switch 206 can remain open longer than the light "on time", allowing a longer settling time for the trans-impedance amplifier 202. The use of a one-stage trans-impedance amplifier 202 is offered by way of example only and is not meant to be restrictive of the present disclosure. In other embodiments, other types of amplifiers or methods of implementation can be used. For example, the trans-impedance amplifier 202 can be implemented in two stages, with a resistor feedback stage followed by a switched-integrator configuration.

As illustrated in FIG. 1A, the gated physiological monitoring system 100 can also include a data converter 130. The data converter 130 can receive at least one of the R-wave 106 timing information from the ECG system 102 or a PPG voltage signal from the PPG monitoring device 108. The data converter 130 can convert the at least one of the R-wave 106 timing information or the PPG voltage signal into digital data associated with the ECG waveform and PPG waveform, respectively. For example, the data converter 130 can include an analog-to-digital converter (ADC) configured to convert the analog signal(s) into discrete or digital data format.

The gated physiological monitoring system 100 can further include control circuitry 132 (e.g., digital back-end circuitry). The control circuitry 132 can include hardware, software, and/or firmware configured to operate the gated physiological monitoring system 100. In some embodiments, control circuitry 132 can include a processor and a memory. The processor can include any number of processors, micro-controllers, or other processing systems (e.g., programmable logic device(s) or the like). The processor is in communication with resident or external memory for storing data and other information accessed or generated by the control circuitry 132. The processor may execute one or more software programs (e.g., modules) from the memory to implement steps, algorithms, operations, or techniques described herein.

The memory can include tangible computer-readable media that provides storage functionality to store various data associated with the operation of the control circuitry 132, such as a software program (e.g., a non-transitory computer-readable medium embodying a program executable by the processor) and code segments mentioned herein, or other data to instruct the processor (and other elements of the control circuitry 132 to perform the steps or operations described herein.

The control circuitry 132 can be communicatively coupled to the data converter 130. The control circuitry 132 can receive digital data corresponding to R-wave timing information and PPG voltage signal from the data converter 130. The processor can compare the digital data received from the data converter 130 and determine timing for the operation of the PPG monitoring device 108 at a PPG measurement site (e.g., the PPG wave upstroke, PPG wave downstroke, etc.). For example, the R-wave timing information or timing information obtained from another physiological measurement can be used to determine a PPG measurement frame, during which the control circuitry 132 can operated the PPG monitoring device 108. In some embodiments, the PPG data can also be used to operate the PPG monitoring device (e.g., as part of a feedback loop).

Figure 3:
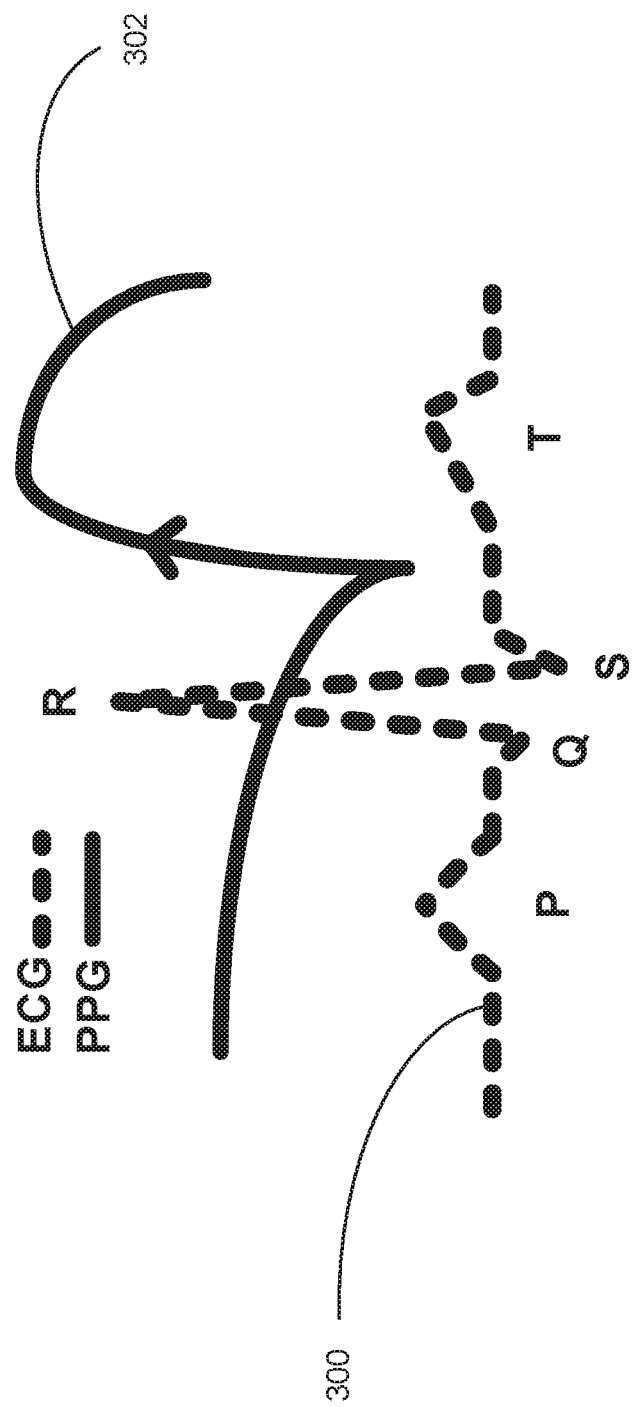
FIG. 3 shows example signals that demonstrate a relationship between an ECG waveform and a PPG waveform.

FIG. 3 illustrates the graphical relationship between the ECG waveform 300 and the PPG waveform 302. The R-wave 106 of the ECG waveform 300 represents ventricular depolarization, which is immediately followed by ventricular contraction. A pulse wave generated from the contraction travels through the artery causing arterial dilation corresponding to the upstroke of the PPG waveform 302. Thus, the R-wave 106 of the ECG always leads to the upstroke of the PPG waveform 302. In some implementations, the control circuitry 132 can be configured to compare and integrate the digital data about the R-wave 106 and the PPG waveform 302 received from the data converter 130.

Figure 4:
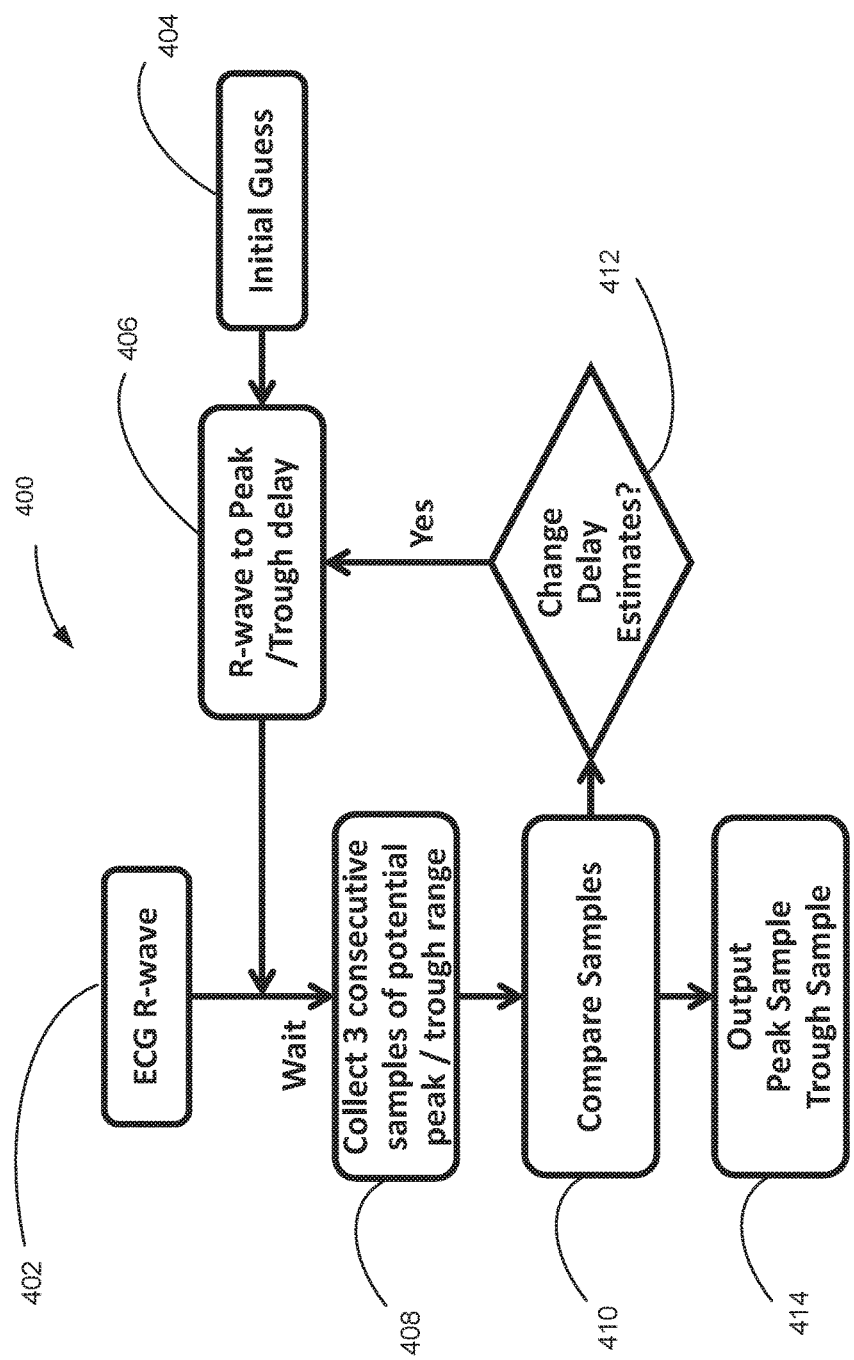
FIG. 4 is a flow diagram of a process for determining a delay between an ECG waveform and a PPG waveform in accordance with implementations of the present disclosure.

FIG. 4 illustrates an example delay search algorithm 400 that can be utilized to integrate the data from the R-wave 106 and the PPG waveform 302. The ECG system 102 is used to obtain the ECG waveform 300 (Block 402). The ECG waveform 300 can be utilized to determine an initial estimate of the timing delay between the R-wave 106 and the PPG waveform 302 (Block 404). The initial estimate of timing delay is used to estimate the PPG wave peak 136 and PPG wave trough 138 (Block 406). In some implementations, the processor can execute a gradient ascent or descent algorithm that utilizes the relationship between the ECG waveform 300 and the PPG waveform 302 to determine the delays between the ECG waveform 300 and the PPG waveform 302. The processor can determine an estimate of the timing of the PPG wave peak 136 and the PPG wave trough 138 (e.g., as identified in FIG. 1D) based on known information about the time delay between the ECG waveform 300 and the PPG waveform 302.

Based on the initial timing estimate, the PPG monitoring device 108 can be operated to obtain non-uniform PPG samples (Block 408). In implementations, the control circuitry 132 can cause the infrared LED driver 116 and red LED driver 118 to propagate the infrared light 116 and red light 114, respectively, to obtain sample PPG wave peaks 136 and PPG wave troughs 138. The obtained PPG samples can then be compared to determine a more accurate time delay (Block 410). The estimated time delay can then be adjusted based on the comparison of the PPG samples (Block 412). In implementations, the control circuitry 132 can be configured to adjust the estimated delay in operation of the PPG monitoring device 100 based on samples of the PPG wave peak 136 and PPG wave trough 138. For example, the processor can cause the PPG monitoring device 100 to obtain three consecutive sample PPG wave peaks 136 and three consecutive sample PPG wave troughs 138. The processor can then compare the obtained samples and adjust the original delay estimate based on the obtained samples. Based on the adjusted time delays, the PPG monitoring device 108 can be operated to obtain increasingly accurate PPG peaks 138 and PPG troughs 140 (Block 414). However, delay search algorithm 400 is offered by way of example only and is not meant to be restrictive of the present disclosure. In other embodiments, alternative sampling algorithms may be used (e.g., increasing or decreasing the number of samples collected). Additionally, the use of control circuitry 132 to integrate the data obtained from the ECG system 102 and the PPG monitoring device 108 is offered by way of example only and is not meant to be restrictive of the present disclosure. In other embodiments, the PPG monitoring device 108 can be manually adjusted in response to data obtained from the ECG system 102.

The processor can utilize the obtained PPG wave peaks 136 and PPG wave troughs 138 to determine the PPG wave upstroke. The control circuitry 132 can then cause the infrared LED driver 120 and red LED driver 122 to propagate the infrared light 116 and red light 114, respectively, during the PPG upstroke. Thus, the control circuitry 132 can assert an enable signal allowing only one light pulse transmission per cardiac cycle during the PPG waveform 302 upstroke for both the infrared LED 112 and the red LED 114, minimizing energy utilization. The processor can implement an algorithm (e.g., ratio of ratios, or the like) to determine SpO2 from the PPG wave upstroke. However, the identification of the PPG wave upstroke is offered by way of example only and is not meant to be restrictive of the present disclosure. It should be understood that similar techniques may be used to detect other portions of the PPG waveform 302 (e.g., downstroke in the PPG waveform 302). Additionally, similar techniques may be utilized to determine one or more additional physiological parameters (e.g., blood pressure, pulse rate, etc.).

In some implementations, the processor can implement operations to reduce noise from environmental interferences (e.g., light from fluorescent lamps, etc.). The processor can execute an algorithm (e.g., fast Fourier transform, or the like) to transform environmental interferences into frequencies. The processor can then compensate for these frequencies in the signal chain. In other implementations, the processor can execute an algorithm (e.g., SNR estimation block) to determine the SNR necessary to achieve a desired level of accuracy in the SpO2 estimation. The processor can then adjust the strength of the LED drivers to maintain the SNR just high enough to achieve the desired level of accuracy.

In some embodiments, the gated physiological monitoring system 100 can be integrated into a mobile device (e.g., smart phone, tablet, media player, or the like) or a wearable device (e.g., activity tracker, smartwatch, or the like). The wearable device can include one or more sensors (e.g., optical sensors, motion sensors, piezoelectric sensors, electrodes, etc.) that can be attached to appropriate portions of the body. A low-energy consumption sensor (e.g., an ECG electrode), can be configured to obtain timing information used to operate a high-energy consumption PPG sensor (e.g., an optical sensor) to measure a physiological parameter by the techniques described herein. However, the use of an electrode sensor paired with an optical sensor is offered by way of example only and is not meant to be restrictive of the present disclosure. In other embodiments, other combinations of sensors can be used. Reducing the energy consumption of the sensors increases the lifetime of the wearable device. In some embodiments, the sensors can be integrated within a wearable garment, adhesive patch, or the like.

The control circuitry 132 can also be implemented in a wearable device. In some implementations, wearable sensors can communicate with a mobile device (e.g., smartphone, tablet, etc.) or another wearable device (e.g., activity tracker, smartwatch, smart bracelet, smart glasses, pedometer, etc.) using wired or wireless connectivity. In some embodiments, the mobile device and/or the wearable device itself can be equipped with a display (e.g., a touch-sensitive panel). The display can be configured to receive user input and display data related to the measured physiological parameter in real time.

Figure 5:
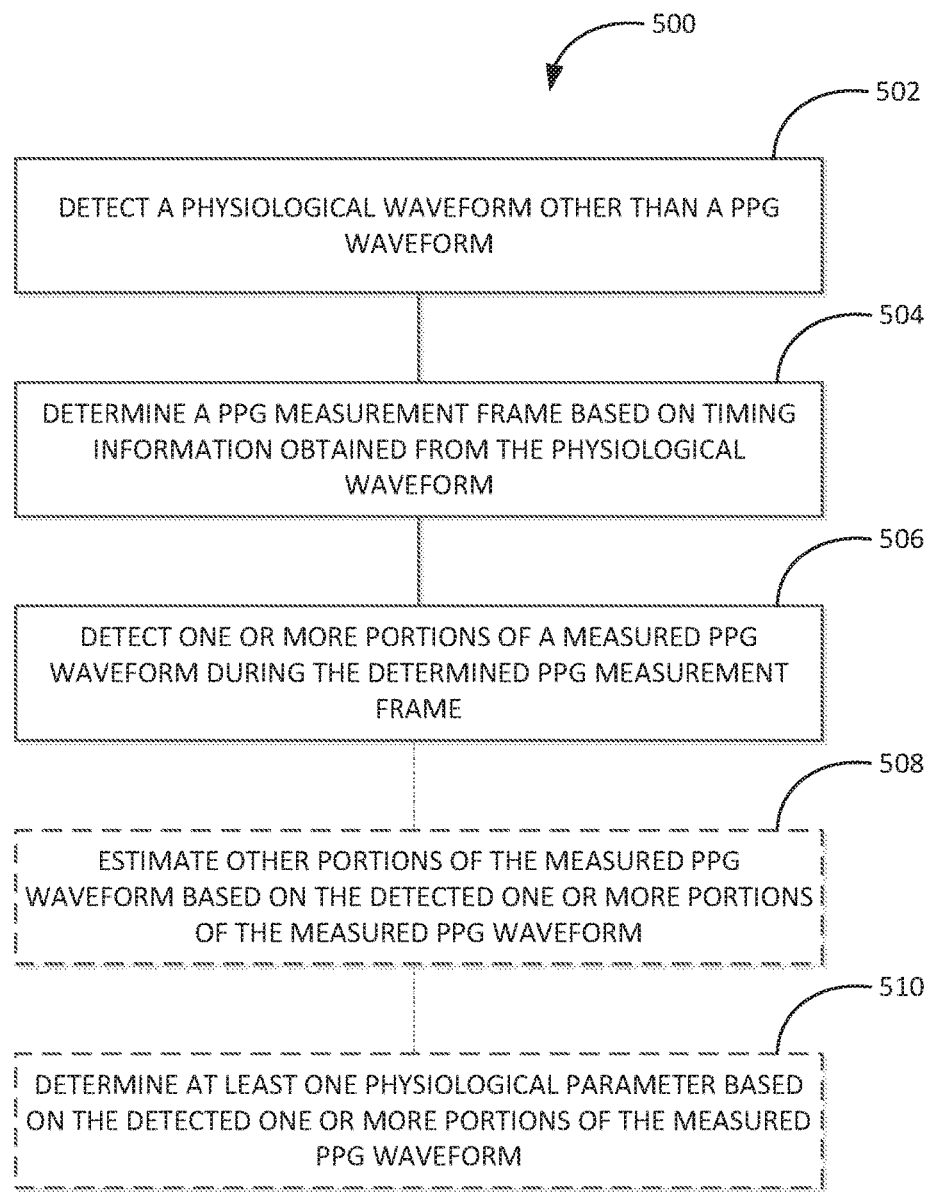
FIG. 5 is a flow diagram of a process for operating a gated physiological monitoring system, such as the gated physiological monitoring system of FIG. 1A, in accordance with implementations of the present disclosure.

FIG. 5 illustrates a method 500 of implementing gated physiological monitoring. In some implementations, method 500 can be manifested by a gated physiological monitoring system, such as the gated physiological monitoring system 100 described herein with reference to FIGS. 1A through 4. Accordingly, system 100 can include components configured to achieve any steps or operations of method 500, and likewise, method 500, in addition to the operations discussed below, can include any steps or operations described herein with regard to system 100.

At block 502, a physiological waveform other than a PPG waveform (e.g., ECG waveform 300) is detected by a physiological monitoring device. In an implementation illustrated in FIG. 1, the physiological monitoring system can be an ECG monitoring system 102. The ECG monitoring system 102 can detect an ECG signal 104. The ECG monitoring system 102 can utilize the QRS complex of the ECG signal 104 to detect the R-wave 106 in the ECG signal 104. The ECG monitoring system 102 (or associated control circuitry) can obtain timing information from the detected R-wave 106. However, the use of an ECG system 102 to detect an R-wave is offered by way of example only and is not meant to be restrictive of the present disclosure. In other embodiments, other physiological waveforms that provide information about arterial pulsation can be used (e.g., ballistocardiogram, impedance cardiogram, etc.).

At block 504, a PPG measurement frame is determined based on timing information from the physiological waveform. In some implementations, the timing information obtained from the physiological waveform is used to estimate a delay between the physiological waveform and a PPG waveform 302. As illustrated in FIG. 4, a delay search algorithm can be used to determine the PPG measurement frame. The R-wave 106 of the ECG signal 104 is used to determine an initial estimate of R-wave 106 to PPG wave peak 136 delay and R-wave 106 to PPG wave trough 138 delay. Based on the initial delay estimate, a PPG monitoring device 108 is operated to obtain non-uniform PPG samples. For example, LED drivers of the PPG monitoring device 108 can drive LEDs to obtain consecutive PPG wave peak 136 and PPG wave trough 138 samples. In some implementations, three PPG peak 138 samples and three PPG trough 140 samples can be obtained. The R-wave 106 to PPG wave peak delay 136 and R-wave 106 to PPG wave trough 138 delay estimates can be adjusted based on comparison of the obtained PPG samples. By adjusting the delay estimates based on non-uniform PPG samples, an increasingly robust and accurate PPG measurement frame can be determined.

At block 506, one or more portions of a measured PPG waveform can be detected during the determined PPG measurement frame. In some implementations, the PPG monitoring device 108 is operated only during the determined PPG measurement frame. For example, the LED drivers of the PPG monitoring device 108 can be duty-cycled so as to operate only following an enable signal from the PPG monitoring device 108 executed based on the adjusted delay estimate.

In some implementations, the method 500 further includes (block 508) estimating other portions of the measured PPG waveform based on the detected on or more portions of the measured PPG waveform. For example, other portions of the measured PPG waveform can be detected by mapping a predetermined PPG curve onto detected portions (e.g., onto a detected peak and trough). In some implementations, the method 500 further includes (block 510) determining at least one physiological parameter (e.g. SpO2, pulse rate, etc.) based on the detected one or more portions of the measured PPG waveform. For example, the detected portions (e.g., peak and/or trough) can be used to detect one or more physiological parameters. In some implementations, the method 500 includes (block 508) estimating other portions of the measured PPG waveform and then determining one or more physiological parameters based on both the estimated portions and detected portions of the measured PPG waveform. In this manner, a full PPG waveform or continuous portion of a PPG waveform can be used for determining physiological parameters with less power consumption because the PPG monitoring device only need to be run during the determined PPG measurement frame to detect selected portions of the PPG waveform (e.g., peak and trough).

Those skilled in the art will appreciate that the forgoing operations can be carried out in any order, unless otherwise indicated herein, and that one or more steps may be carried out substantially simultaneously or at least partially in parallel. It should be further recognized that the various functions, operations, blocks, or steps described throughout the present disclosure may be carried out by any combination of hardware, software, or firmware. Various steps or operations may be carried out by control circuitry including one or more of the following: electronic circuitry, logic gates, multiplexers, a programmable logic device, an application-specific integrated circuit (ASIC), a controller/microcontroller, or a computing system. A computing system may include, but is not limited to, a personal computing system, mainframe computing system, workstation, image computer, parallel processor, or any other device known in the art. In general, the terms "control circuitry," "controller," and "computing system" are broadly defined to encompass any device having one or more processors, which execute instructions from a carrier medium.

Program instructions implementing methods, such as those manifested by embodiments described herein, may be transmitted over or stored on carrier medium. The carrier medium may be a transmission medium, such as, but not limited to, a wire, cable, or wireless transmission link. The carrier medium may also include a non-transitory signal bearing medium or storage medium such as, but not limited to, a read-only memory, a random access memory, a magnetic or optical disk, a solid-state or flash memory device, or a magnetic tape.

It is further contemplated that any embodiment or implementation of the disclosure manifested above as a system or method may include at least a portion of any other embodiment or implementation described herein. Those having skill in the art will appreciate that there are various embodiments or implementations by which systems and methods described herein can be implemented, and that the implementation will vary with the context in which an embodiment of the disclosure is deployed. Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A gated physiological monitoring system, comprising:
   a physiological monitoring device configured to produce a physiological waveform other than a photoplethysmogram (PPG) waveform;

a PPG monitoring device configured to obtain a PPG measurement following an implementation of a measurement timing delay upon detection of a characteristic of the physiological waveform; and a control circuitry communicatively coupled to the physiological monitoring device and to the PPG monitoring device and configured to:

obtain a sample physiological waveform via the physiological monitoring device, generate an estimated timing delay between a characteristic of the sample physiological waveform and a known characteristic of the PPG waveform, obtain at least two consecutive sample PPG waveforms via the PPG monitoring device based on the estimated timing delay, and generate the measurement timing delay based on the estimated timing delay and the at least two consecutive sample PPG waveforms.

2. The gated physiological monitoring system of claim 1, wherein the physiological monitoring device comprises at least one of an electrocardiogram (ECG) monitoring device, a ballistocardiogram monitoring device, and an impedance cardiogram monitoring device.

3. The gated physiological monitoring system of claim 1, wherein the PPG monitoring device further includes at least one LED driver configured to operate upon the implementation of the measurement timing delay following the detection of the characteristic of the physiological waveform.

4. The gated physiological monitoring system of claim 1, further comprising a data converter in communication with at least one of the physiological monitoring device and the PPG monitoring device.

5. The gated physiological monitoring system of claim 1, wherein the control circuitry comprises:

a memory configured to store one or more modules; and a processor coupled to the memory, the processor being configured to execute the one or more modules that cause the processor to receive data from the physiological monitoring device and the PPG monitoring device.

6. The gated physiological monitoring system of claim 1, wherein the control circuitry is further configured to determine a PPG measurement frame based on the measurement timing delay and the characteristic of the physiological waveform.

7. The gated physiological monitoring system of claim 6, wherein the control circuitry is further configured to operate the PPG monitoring device during the determined PPG measurement frame to obtain the PPG measurement.

8. The gated physiological monitoring system of claim 1, wherein the control circuitry is further configured to estimate portions of a PPG waveform based on the obtained PPG measurement.

9. The gated physiological monitoring system of claim 1, wherein the control circuitry is further configured to determine at least one physiological parameter based on the PPG measurement.

10. The gated physiological monitoring system of claim 1, wherein the control circuitry is further configured to determine an oxygen saturation physiological parameter based the PPG measurement.

11. A gated physiological monitoring system, comprising:

a physiological monitoring device configured to produce a physiological waveform other than a photoplethysmogram (PPG) waveform;

a PPG monitoring device configured to obtain a PPG measurement during a PPG measurement frame; and control circuitry in communication with the physiological monitoring device and the PPG monitoring device, the control circuitry including:

a memory configured to store one or more modules; and a processor coupled to the memory, the processor being configured to execute the one or more modules that cause the processor to:

obtain a sample physiological waveform via the physiological monitoring device, generate an estimated timing delay between a characteristic of the physiological waveform and a known characteristic of the PPG waveform, obtain at least two consecutive sample PPG waveforms via the PPG monitoring device based on the estimated timing delay, and generate a measurement timing delay based on the estimated timing delay and the at least two consecutive sample PPG waveforms, detect a measured physiological waveform other than the PPG waveform via the physiological monitoring device, identify a characteristic of the measured physiological waveform corresponding to the characteristic of the sample physiological waveform, determine the PPG measurement frame based on measured physiological waveform and the measurement timing delay, and operate the PPG monitoring device during the determined PPG measurement frame to detect one or more portions of a PPG waveform.

12. The gated physiological monitoring system of claim 11, wherein the processor is configured to execute the one or more modules to cause the processor to determine an oxygen saturation physiological parameter based on the detected one or more portions of the PPG waveform.

13. A method for gated physiological monitoring, comprising:

generating a measurement timing delay, the generating of the measurement timing delay comprising:

obtaining a sample physiological waveform other than a photoplethysmogram (PPG) waveform via a physiological monitoring device;

generating an estimated timing delay between a characteristic of the sample physiological waveform and a known characteristic of the PPG waveform;

obtaining at least two consecutive sample PPG waveforms via the PPG monitoring system based on the estimated timing delay; and generating a measurement timing delay based on the estimated timing delay and the at least two consecutive sample PPG waveforms;

detecting a physiological waveform other than the PPG waveform via the physiological monitoring device identifying a characteristic of the detected physiological waveform corresponding to the characteristic of the sample physiological waveform;

determining a PPG measurement frame based on the characteristic of the detected physiological waveform and the measurement timing delay; and detecting one or more portions of a PPG waveform during the PPG measurement frame via the PPG monitoring system.

14. The method of claim 13, wherein the physiological waveform comprises at least one of an ECG waveform, a ballistocardiogram waveform, and an impedance cardiogram waveform.

15. The method of claim 13, wherein the physiological waveform is detected with an ECG monitoring device.

16. The method of claim 13, wherein the one or more portions of the PPG waveform are detected by operating at least one LED driver of a PPG monitoring device during the PPG measurement frame.

17. The method of claim 13, further comprising:
   estimating other portions of the PPG waveform based on the detected one or more portions of the PPG waveform.

18. The method of claim 13, further comprising:
   determining at least one physiological parameter based on the detected one or more portions of the PPG waveform.

19. The method of claim 13, further comprising:
   determining a oxygen saturation physiological parameter based on the detected one or more portions of the PPG waveform.

20. The gated physiological monitoring system of claim 11, wherein the processor is configured to execute the one or more modules to cause the processor to determine at least one physiological parameter based on the detected one or more portions of the PPG waveform.

\* \* \* \* \*